(12) United States Patent
Epley

(10) Patent No.: US 7,840,260 B2
(45) Date of Patent: Nov. 23, 2010

(54) IONTOPHORETIC INTRA-TYMPANIC DRUG DELIVERY SYSTEM

(75) Inventor: John M. Epley, Portland, OR (US)

(73) Assignee: Yainax Medical, LLC, Portland, OR (US)

( * ) Notice: Subject to any disclaimer, the term of this patent is extended or adjusted under 35 U.S.C. 154(b) by 164 days.

(21) Appl. No.: 12/012,109

(22) Filed: Jan. 30, 2008

(65) Prior Publication Data
US 2008/0132824 A1 Jun. 5, 2008

Related U.S. Application Data

(62) Division of application No. 11/039,556, filed on Jan. 20, 2005, now Pat. No. 7,351,246.

(60) Provisional application No. 60/538,077, filed on Jan. 20, 2004.

(51) Int. Cl.
*A61N 1/30* (2006.01)
*A61F 11/00* (2006.01)
(52) U.S. Cl. .......................... 604/21; 606/109
(58) Field of Classification Search ............ 604/21, 604/35, 239, 275, 514; 606/109
See application file for complete search history.

(56) References Cited

U.S. PATENT DOCUMENTS

| | | | |
|---|---|---|---|
| 3,645,208 A * | 2/1972 | Weinssen et al. ............ | 102/513 |
| 3,645,268 A * | 2/1972 | Capote ....................... | 604/117 |
| 3,991,755 A * | 11/1976 | Vernon et al. ................ | 604/20 |
| 4,034,759 A | 7/1977 | Haerr | |
| 4,334,538 A | 6/1982 | Juhn | |
| 4,585,446 A * | 4/1986 | Kempf ....................... | 604/274 |
| 5,057,082 A * | 10/1991 | Burchette, Jr. ......... | 604/164.06 |
| 5,405,321 A | 4/1995 | Reeves | |
| 5,421,818 A | 6/1995 | Arenberg | |
| 5,474,529 A | 12/1995 | Arenberg | |

(Continued)

OTHER PUBLICATIONS

Wearne et al., "Control of Spatial Orientation of the Angular Vestibuloocular Reflex by the Nodulus and Uvula", J. Neurophysiol. 79:2690-2715 (1998).

*Primary Examiner*—Kevin C Sirmons
*Assistant Examiner*—Andrew M Gilbert
(74) *Attorney, Agent, or Firm*—James G. Stewart PC

(57) ABSTRACT

A system, method, and apparatus for iontophoretically delivering medically-active ions beyond the tympanic membrane, into a middle ear portion of a patient, and to an area or structure of the middle or inner ear that is targeted for treatment. The system and apparatus can include a needle configured partially for insertion through a tympanic membrane and having a longitudinal bore, a flexible lumen coupled with the needle, and typically a fluid source coupled with the lumen such that a fluid in the fluid source can be delivered from the fluid source, through the lumen and the needle, and into the middle ear. A positioning tab can be coupled with the needle to assist determining a proper insertion extent of the needle through the membrane. The system and method can also include a power source having oppositely charged electrodes, electrically-conductive materials coupled with an electrode and disposed within the fluid source, lumen, and/or needle, and electrically-conductive materials coupled with an oppositely-charged electrode and further coupled with the patient's skin. Medically-active ions are iontophoretically delivered by the apparatus, when the fluid is delivered to a patients middle ear and an electrical charge is imparted to the ions by the apparatus.

18 Claims, 9 Drawing Sheets

U.S. PATENT DOCUMENTS

| | | |
|---|---|---|
| 5,476,446 A | 12/1995 | Arenburg |
| 5,674,196 A * | 10/1997 | Donaldson et al. ....... 604/93.01 |
| 6,045,528 A * | 4/2000 | Arenberg et al. ............... 604/28 |
| 6,124,484 A | 9/2000 | Silverstein |
| 6,256,533 B1 * | 7/2001 | Yuzhakov et al. ............. 604/21 |
| 6,368,315 B1 | 4/2002 | Gillis et al. |
| 6,377,849 B1 * | 4/2002 | Lenarz et al. ................. 604/21 |
| 6,440,102 B1 | 8/2002 | Arenberg et al. |
| 6,648,873 B2 | 11/2003 | Arenberg et al. |
| 6,685,697 B1 | 2/2004 | Arenberg et al. |
| 6,770,080 B2 | 8/2004 | Kaplan et al. |
| 7,044,942 B2 * | 5/2006 | Jolly et al. ................ 604/891.1 |
| 7,044,962 B2 | 5/2006 | Elliott |
| 7,351,246 B2 * | 4/2008 | Epley ......................... 606/109 |
| 2004/0097839 A1 * | 5/2004 | Epley ......................... 600/595 |
| 2005/0154434 A1 * | 7/2005 | Simon et al. ................. 607/116 |
| 2007/0167918 A1 | 7/2007 | Reed et al. |
| 2008/0262468 A1 * | 10/2008 | Clifford et al. .............. 604/501 |
| 2008/0262508 A1 * | 10/2008 | Clifford et al. .............. 606/109 |
| 2008/0262509 A1 * | 10/2008 | Clifford et al. .............. 606/109 |
| 2008/0262510 A1 * | 10/2008 | Clifford ...................... 606/109 |
| 2009/0163848 A1 * | 6/2009 | Morriss et al. ................ 604/20 |
| 2010/0030131 A1 * | 2/2010 | Morriss et al. ................ 604/21 |

* cited by examiner

IONTOPHORETIC INTRA-TYMPANIC DRUG DELIVERY SYSTEM

RELATED APPLICATIONS

This application is a divisional of and claims the benefit of priority to U.S. Non-Provisional patent application Ser. No. 11/039,556, filed on Jan. 20, 2005 and entitled MINIMALLY INVASIVE, SUSTAINED, INTRA-TYMPANIC DRUG DELIVERY SYSTEM, now U.S. Pat. No. 7,351,246, which itself claims the benefit of priority to U.S. Provisional patent application No. 60/538,077 filed on Jan. 20, 2004 and entitled COMPACT, PUMPING-CONTROLLED, TRANS-TYMPANIC-MEMBRANE, LIQUID DRUG DELIVERY, the contents of which are hereby incorporated herein in their entirety by this reference.

FIELD OF THE INVENTION

The invention relates generally to the field of treatment for middle and/or inner ear disorders. More particularly, the invention relates to an apparatus, system, and method for effectively delivering drugs beyond (medially relative to) a tympanic membrane of a patient's ear.

BACKGROUND OF THE INVENTION

This invention relates to an apparatus and method for the compact, selectively controlled and metered introduction of a medical fluid, such as a drug, through the tympanic membrane and into the middle ear of a patient.

It is desirable in certain circumstances to administer medications or other medical fluids into the middle ear through the tympanic membrane. Intratympanic perfusion of drugs for treatment of inner ear conditions was popularized the 1970's in Europe with the treatment of Meniere's disease with intratympanic aminoglycoside antibiotics. This route of administration has since gained wider utilization in the treatment of many other ear conditions as well, including tinnitus, sudden hearing loss, and various forms of labyrinthine dysfunction. Medications typically used include aminoglycosides, corticosteroids and local anesthetics. Anticipated delivery of other medications by this route has undergone widespread discussion.

Intratympanic delivery of drugs has been accomplished in the past principally by making a small incision in the anesthetized tympanic membrane (ear drum), inserting a needle or catheter into the middle ear, infusing the drug in liquid form and allowing it to be absorbed into the inner ear, probably mainly by way of the round window membrane. Other methods have included placing an incision or implanted tube in the tympanic membrane and then having the patient self-dispense the drug into the external ear canal whereby it is intended to pass through the opening into the middle ear, and thence the inner ear. This has the disadvantage that infectious debris can be carried into the middle ear from the external canal, with the risk of creating a middle ear infection, and passage of the liquid into the middle ear is inhibited by the surface tension of the liquid. These problems have been partially solved by inserting a wick between the external ear canal and the middle ear, as in U.S. Pat. No. 6,120,484 to Silverstein. But this method has the disadvantages of possible patient noncompliance, errors in following directions, confusion of medications, failure of some or all of the instilled drops to reach the wick and chronic perforations due to the extended use of the wick.

U.S. Pat. No. 5,474,529 to Arenburg describes a multifunctional inner ear treatment and diagnostic system, using a two channel catheter that leads to a small reservoir placed in the round window niche and connected with the round window membrane via small openings through which the drug is allowed to diffuse. Implantation is difficult, and the large catheter often leaves a defect in the tympanic membrane.

Other examples of apparatus and methods for accomplishing intratympanic drug delivery are described, for example, in U.S. Pat. Nos. 4,034,759, 5,421,818, 5,474,529, 5,476,446, 6,368,315, 6,440,102 and 6,685,697.

Recent studies have shown that there is a blood-labyrinth barrier similar to the blood-brain barrier, such that very little of most medications delivered systemically (oral, IV, etc.) is transported to the inner ear. Thus, to accomplish a therapeutic concentration of the medication within the inner ear when delivered via the systemic route, high concentrations of the medication over sustained periods of time are necessary, increasing the risk of systemic side effects.

On the other hand, if a solution containing the drug molecules is placed into the middle ear and is allowed to remain for a period of time, a small portion of the molecules will be absorbed into the inner ear, probably mainly by diffusion through the round window membrane. The amount of absorption of the drug molecules through the round window, and hence the dose of the drug reaching the inner ear structures, is proportional to the concentration of the drug in contact with the round window membrane, and the time the drug remains in contact with the round window membrane at said concentration.

The middle ear cavity can hold approximately 0.5 cc of fluid. Its outer surface is lined by a mucous membrane, which absorbs medication molecules from the middle ear. If a solution (perfusate) containing medication is thus placed in the middle ear cavity, the molecules of that medication in the solution will diffuse over time into the surrounding tissues, including the round window membrane. The round window represents only a small proportion (less than 2%) of surface area of the surrounding tissues. Therefore only a small portion of the molecules of drug will diffuse through the round window into the inner ear. On the other hand, the volume of the inner ear is only about 1 cc, so that relatively few molecules of medication are needed to obtain a therapeutic concentration in the inner ear. Molecules of drug diffuse out of the solution into the surrounding tissues so that concentration of drug in the solution becomes less with time, following an asymptotic curve. The applicant's studies indicate that the half-life of drug molecules (i.e., time until one-half of the quantity of drug is depleted) in the solution in the middle ear is approximately 5 minutes. Thus, if the typical protocol for single injection is followed, and 0.5 cc of a drug is infused into the middle ear and allowed to remain for 30 minutes, the concentration of the drug in the middle ear becomes quite low during last 15-20 minutes.

What is desired is an apparatus that is easily used, is capable of controlled administration of fluids into the ear, is stable and comfortable, and which is easily inserted and removed with minimal damage to the tympanic membrane.

DETAILED DESCRIPTION OF THE PREFERRED EMBODIMENTS

Figure 1:
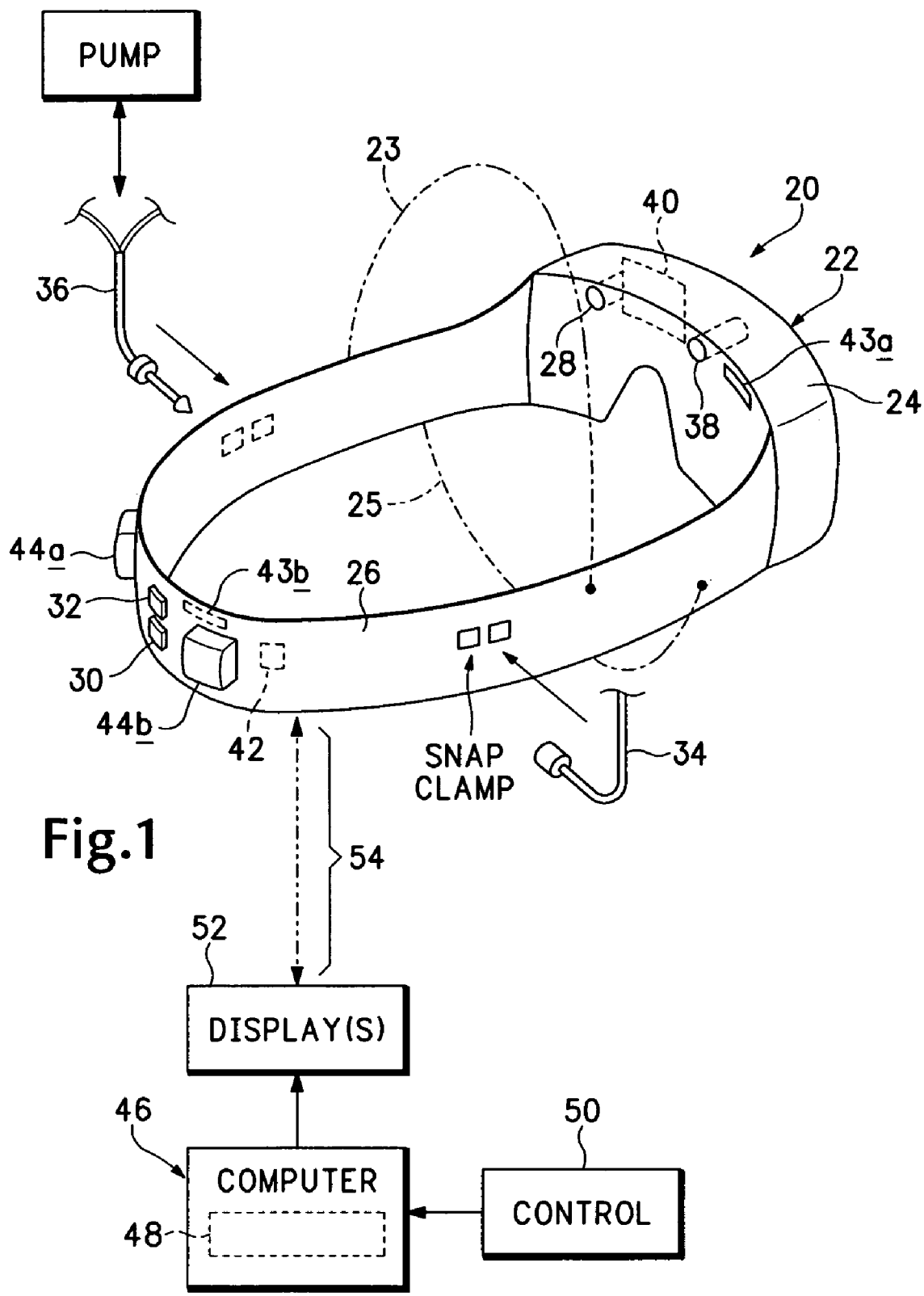
FIG. 1 is an isometric view of a stabilizing headgear of an aspect of the invention.

This invention is an intra-tympanic apparatus comprising a) a needle having a sharpened end adapted to pierce the tympanic membrane of an ear and a distal end, the needle having at least one longitudinal bore having a fluid outlet proximate to the sharpened end for delivering fluid to or removing fluid from the middle ear through the needle and a fluid inlet proximate to the distal end; b) a flexible lumen being in fluid communication with the fluid inlet proximate to the distal end of the needle; c) means for delivering a controllable amount of a fluid into the middle ear through the flexible lumen and the needle; and d) means for removing fluids from the middle ear through the needle.

In another aspect, this invention is an intra-tympanic apparatus comprising a) a needle having a sharpened end adapted to pierce the tympanic membrane of an ear and a distal end, the needle having at least one longitudinal bore having a fluid outlet proximate to the sharpened end for delivering fluid to or removing fluid from the middle ear through the needle and a fluid inlet proximate to the distal end; b) a flexible lumen being in fluid communication with the fluid inlet proximate to the distal end of the needle, wherein the sharpened end of the needle is adapted to form multiple incisions in the tympanic membrane that extend radially from a central point to form multiple flaps in the tympanic membrane.

This invention is also a process for delivering fluid to or removing fluid from the middle ear, comprising; a) puncturing a tympanic membrane of an ear with a needle having a sharpened end adapted to pierce the tympanic membrane and a distal end, wherein 1) the needle has at least one longitudinal bore having a fluid outlet proximate to the sharpened end for delivering fluid to or removing fluid from the middle ear and a fluid inlet proximate to the distal end; and 2) a flexible lumen is in fluid communication with the fluid inlet proximate to the distal end of the needle; b) securing the needle in place such that the sharpened end and the fluid outlet extend into the middle ear and at least a portion of the flexible lumen extends outwardly from the tympanic membrane; and c) delivering at least one fluid to or removing at least one fluid from the middle ear through the fluid outlet of the needle.

The present invention represents a significant and substantial advance in middle and inner ear treatment. Use of the invention enables a multiplicity of therapeutic measures to be readily accomplished using an undemanding design of components and minimally invasive surgical procedures. Specifically, the various embodiments of the invention set forth herein enable: (1) the delivery of vestibulo-active, cochleoactive and osmotically-active liquid therapeutic agents via the middle ear to the inner ear structures; (2) the controlled, relatively clog-free, active and passive withdrawal of fluids of intrinsic and extrinsic origin from the middle ear space, (3) maximal dose available to the inner ear within a short period of time, so as to provide complete treatment in-office, (4) minimization of systemic side effects by limiting systemic absorption of therapeutic medication beyond the ear structures, (5) avoidance of direct contact of components with inner ear structures and thus less risk of damaging the inner ear structures, (6) enhanced absorption and/or diffusion into the inner ear of medication through iontophoretic application, (7) the delivery of therapeutic agents to middle ear structures, and (8) easy, fast and minimally-invasive insertion and removal of components in a simple setting.

An opening to the middle ear is created in the tympanic membrane, and a liquid-passage port structure is established in this opening. This port structure can possess any suitable configuration, and may be either permanently, or only temporarily, installable.

A fluid conduit structure is appropriately coupled disconnectably to the port structure, and is connected, at a location which is upstream from the port structure relative to the membrane, to a small selectively controllable metering pump. This pump in turn, is connected to a suitable reservoir containing the liquid substance which is to be introduced into the middle ear.

The fluid conduit structure, the pump, and the reservoir are small, are comfortably wearable by a patient, and may be located (1) external to the ear, and effectively "hung", or mounted, on the ear, "hearing-aid" style; (2) external to the ear and mounted on stabilizing headgear; or (3) entirely as a miniaturized assembly within the ear, per se.

Liquid delivery may be controlled in any suitable fashion, as by (1) controlled-flow steady stream; (2) pulsed delivery in accordance with a selectable pulse "pattern"; or (3) manually.

Computer control structure, greatly minimized, and preferably programmable, may be included for flow-control purposes.

Figure 2:
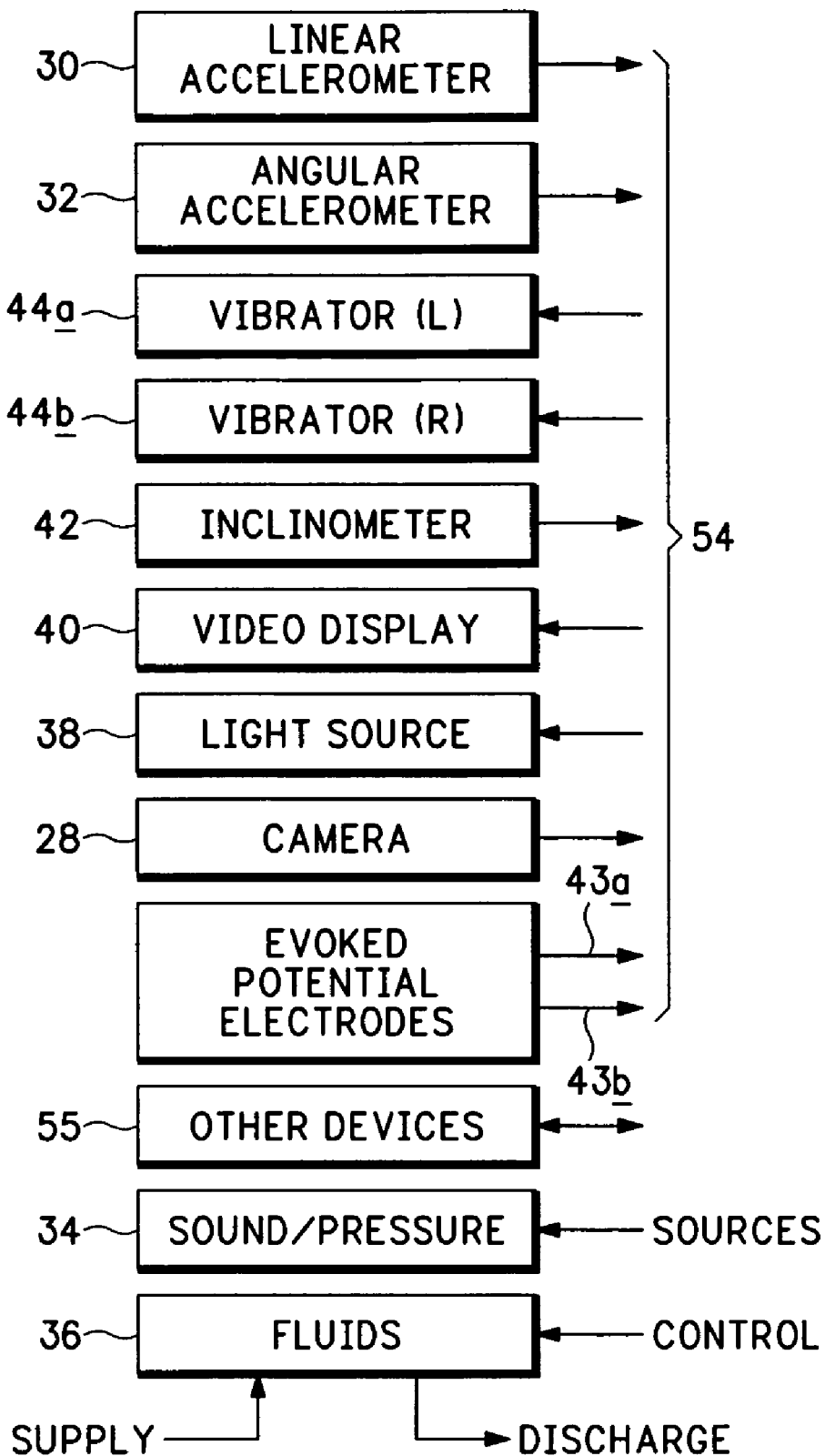
FIG. 2 is a flow chart identifying optional features of the invention.

Turning now to the drawings, and beginning first with reference to FIGS. 1 and 2, indicated generally at 20 in FIG. 1 is one form, and collection, of apparatus constructed and useable in accordance with a preferred implementation of, and manner of practicing, in a best-known mode, the present invention. Apparatus 20, as illustrated in FIG. 1, takes the form of a goggle-like frame structure 22 which includes an eye-bridging housing structure, or housing 24, and a headwrap band 26 which extends from housing 24 in a loop that enables the frame structure to be secured appropriately, in a goggle-wearing fashion, to and around a human subject's head. Band 26 is preferably length-adjustable (in any suitable manner which is not specifically illustrated herein) to enable appropriate and comfortable tightening around the head, is preferably formed of a relatively configurationally stable plastic material, such as a medical-grade polycarbonate material, and may have all, or a portion, of its inner surface equipped appropriately, if so desired, with any suitable high-friction material, such as silicone rubber. Whether or not such a friction material is employed is completely a matter of choice, it only being important, in accordance with the structure and practice of this invention, that when this frame structure is "installed" in a secured condition on a subject's head, it will effectively occupy a condition thereon of substantially complete stability with respect to no relative motion being permitted between the frame structure and the head under normal subject head-motion conditions.

While frame structure 22 is shown as simply involving the two components specifically illustrated and mentioned, it can clearly be modified, if so desired, with other stabilization features, such as an additional strap which might have opposite ends joined to band 26 to extend adjustably and tightenably over the crown of the head, as suggested by dash-dot line 23. It might further include, also if so desired, additional stabilization provided by something in the nature of a conventional, tightenable and adjustable under-the-chin strap, as suggested by dash-dot line 25, and by the previously mentioned ear canal insert.

As has been mentioned earlier herein, practice of an embodiment of the present invention contemplates the selective simultaneous use of plural (at least two at a given time) devices, appropriately anchored to frame structure 22 for the purpose of either collecting data from a subject relative to vestibular behavior (sensors), and/or delivering stimuli to a subject (stimuli deliverers). A representative (but non-exhaustive) list of such devices is now presented, and each of these different kinds of devices is illustrated just very simply and schematically in FIG. 1 in place at a representative selected location on structure 22. Thus, the illustrated devices include a small infrared video camera, or electronic video-image collecting device, 28 which is suitably positioned inside housing 24, a three-axis linear accelerometer 30, a three-axis angular accelerometer 32, a combined sound deliverer and air-pressure modifier 34 (stimuli deliverers), a device 36, referred to herein as fluid-flow structure, for delivering selected fluids/liquids to the ear (also a stimulus deliverer), a suitable, selected light source, or light-emitting structure, 38 which is also mounted inside of housing 24, a small video screen, or visual image-presenting structure, 40 which is disposed within housing 24, an inclinometer 42, a pair of spaced evoked-potential electrodes 43a, 43b, and two (left and right) vibration-generating structures, or vibrators, 44a, 44b, respectively (also referred to as stimuli deliverers).

Fragmentarily illustrated fluid-flow structure 36, only one of which is shown in FIG. 1, could be used in combination with a second such device on the opposite side of band 26, thus to deliver stimuli and/or treatment fluids (liquids) selectively to both ears if desired.

Further with respect to devices 34, 36, while these particular kinds of devices may take a number of different forms, certain preferred, specific constructions for these devices have been found to work especially well in the environment of the present invention, and these specific constructions are illustrated and described herein also, and are specifically discussed a bit later in this text.

At the bottom of FIG. 2 there is a block which is labeled FLUIDS, and this represents a source and return reservoir of fluids supplied to and drawn away from, as appropriate, device 36 when that device is being employed as a fluid-flow structure. A single-headed arrow pointing into the right side of this block, labeled CONTROL, reflects a connection through the communication structure to computer 46, whereby this computer, monitoring nystagmus behavior in a subject, is enabled to control the delivery of fluids, for example, to one of a subject's ears via device 36.

Figure 3:
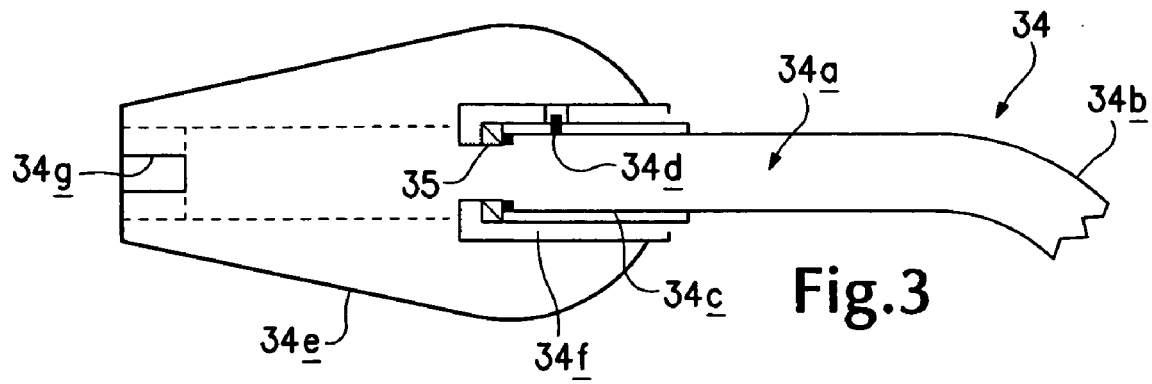
FIG. 3 is a side view, in section, of a combined sound deliverer and air-pressure modifier device.
Figure 3A:
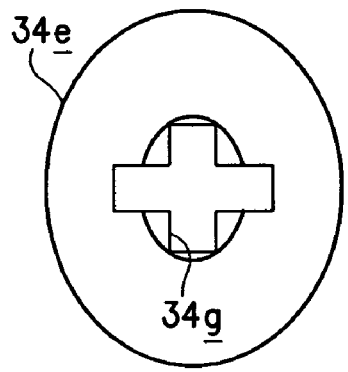
FIG. 3A is an enlarged end view of a tip for a combined sound deliverer and air-pressure modifier device as shown in FIG. 3.

As was mentioned earlier, I have found that there are certain specific structures for devices 34, 36 which work especially well in the headgear-apparatus setting of the present invention. FIGS. 2, 3 and 3A illustrate a preferred construction for a combined sound deliverer and air-pressure modifier device, such as device 34.

Combined device 34 includes an elongate tubular body structure 34a, which may be furnished with a generally right angle bend as is shown at 34b, and which may be made of a relatively rigid plastic material, with this tubular body including what is referred to herein as a delivery end 34c inwardly from which there is provided an outwardly projecting nubbin 34d. Fitted removeably and replaceably on this outer body end is a soft and pliable, typically rubber-like oblong and tapered bulb 34e which is fitted with a mounting structure 34f that enables removable, nubbin-locked positioning of the bulb on body end 34c. Bulb includes an outer exposed end possessing a cross-shaped non-occluding fluid-passage aperture 34g. A washer 35 provides sealing engagement between bulb 34e and body end 34c.

The non-illustrated end of tubular body 34a, during use of this device, is suitably coupled to a source of selected sound, or to a source which enables plus and minus varying of air-pressure under circumstances with body end 34c and bulb 34e suitably inserted into a subject's ear. The soft and pliable nature of bulb 34e, when engaged with ear tissue, produces effectively a fluid tight seal with this tissue which enables the development of pressures both above and below atmospheric pressure. It also provides a relatively good acoustical seal against the introduction of extraneous noise to the ear under circumstances where it is intended that a specific sound be delivered to the ear or ears.

Figure 4:
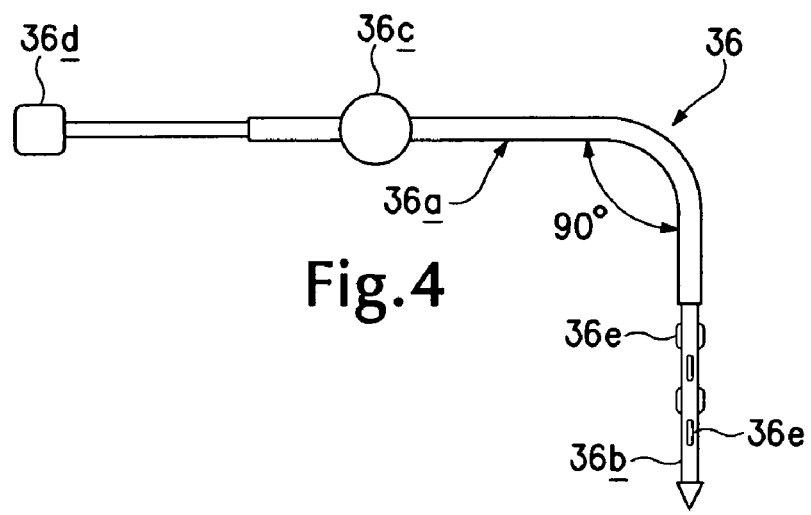
FIG. 4 is a side view of an intra-tympanic apparatus of one embodiment of the invention.
Figure 5:
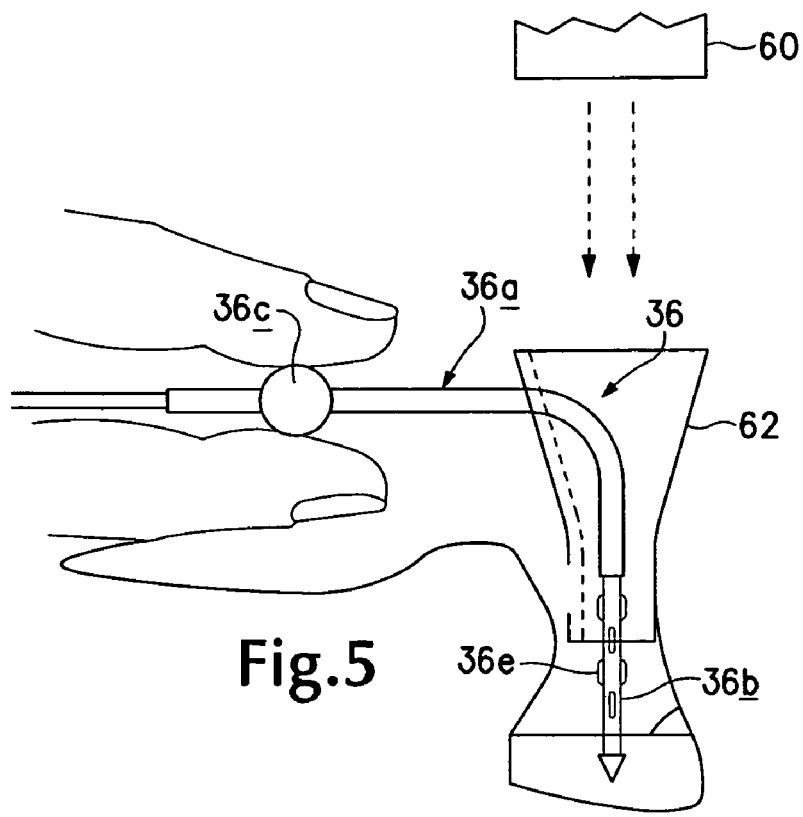
FIG. 5 is a side view, partially in section, illustrating the placement and use of an embodiment of the invention.
Figure 6:
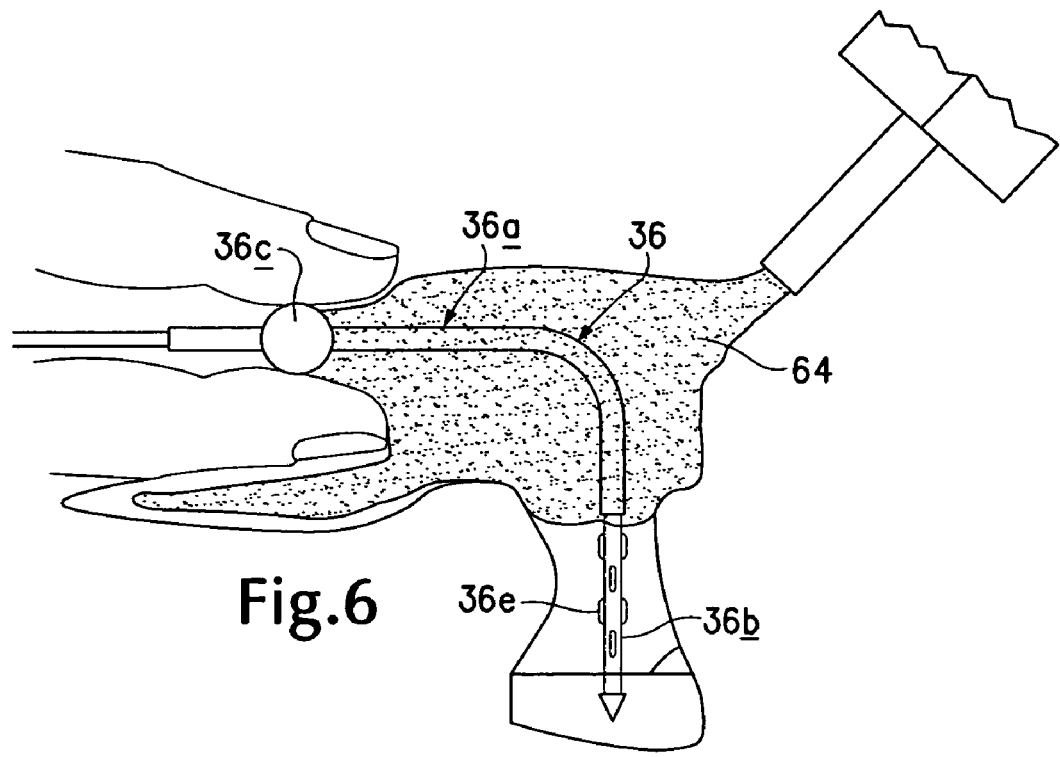
FIG. 6 is a side view, partially in section, illustrating a method of securing an embodiment of the invention in place within the ear canal of a patient.

FIGS. 4-6, inclusive, illustrate a preferred embodiment and manner of utilizing a structure such as fluid-flow structure 36. In general terms, this preferred structure includes an elongate tubular and malleable body 36a which is either formed with, or provided with, a removably attachable, outer trocar end 36b having the evident sharpened structure which permits selective piercing and penetration of the tympanic membrane as is illustrated in FIG. 5. Leading to the trocar is a compliant, easily bendable tube designed to absorb noise and shock imparted inadvertently from the body portion. Malleability in the body enables changeable formation of the bend in the body to accommodate appropriate positioning of trocar end 36b when device 36 is anchored to frame structure 22.

Suitably provided on body 36a, at a location which is somewhat distant from the trocar equipped end of the device, is an enlargement which provides what is referred to herein as a manipulation bead 36c that permits digital manipulation conveniently of this device during insertion, and during stabilization while readying and applying fixation molding material, or other fixating material, such as is illustrated in FIGS. 5 and 6. Just on the opposite side of bead 34c is an appropriate connector 36d which permits connection of one or more appropriately provided fluid lumens within body 36a to a suitable source and reservoir for delivery and return of fluid. For example, a delivery lumen might be connected to the source of a particular liquid drug which is intended to be delivered into the ear during a vestibular-examination procedure.

Figure 7:
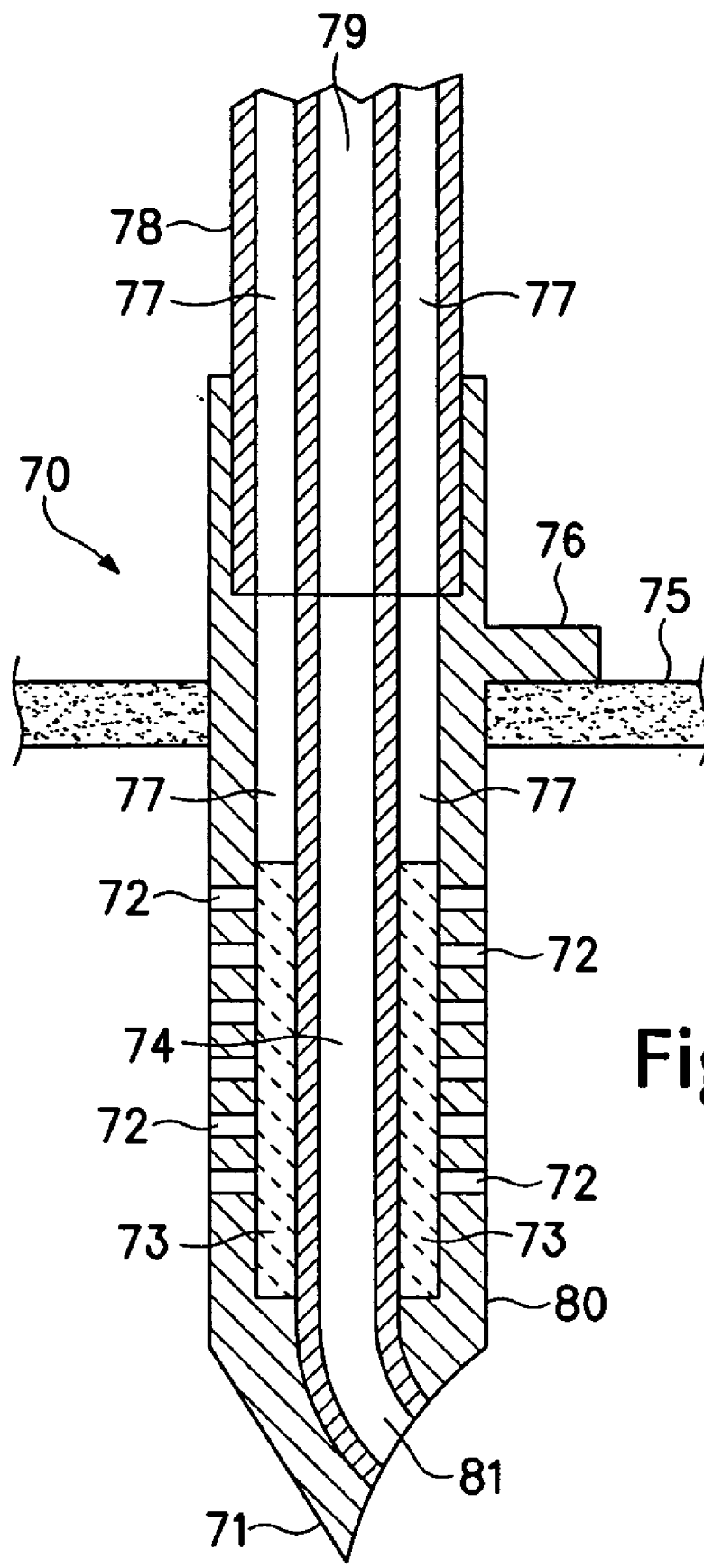
FIG. 7 is an enlarged side sectional view of an embodiment of the invention.

A design with various preferred features is illustrated in FIG. 7. In FIG. 7, device 70 includes needle 80 having tip 71 and fluid outlet 81. Fluid outlet 81 is in fluid communication with bore 74, which in turn is in fluid communication with lumen 79 of catheter 78. Fluids are delivered to the middle ear through lumen 79, central bore 74 and outlet 81. Needle 80 further includes multiple inlets 72, through which fluids can be withdrawn from the middle ear. Withdrawn fluids are drawn past optional filters 73 into lumen 77 within catheter 78. As shown, lumens 77 and 79 are arranged coaxially. Device 70 further includes positioning tab 76 which, when the device is inserted, will contact tympanic membrane 75 and act as a stop, helping to locate the device in its correct position.

Figure 10A:
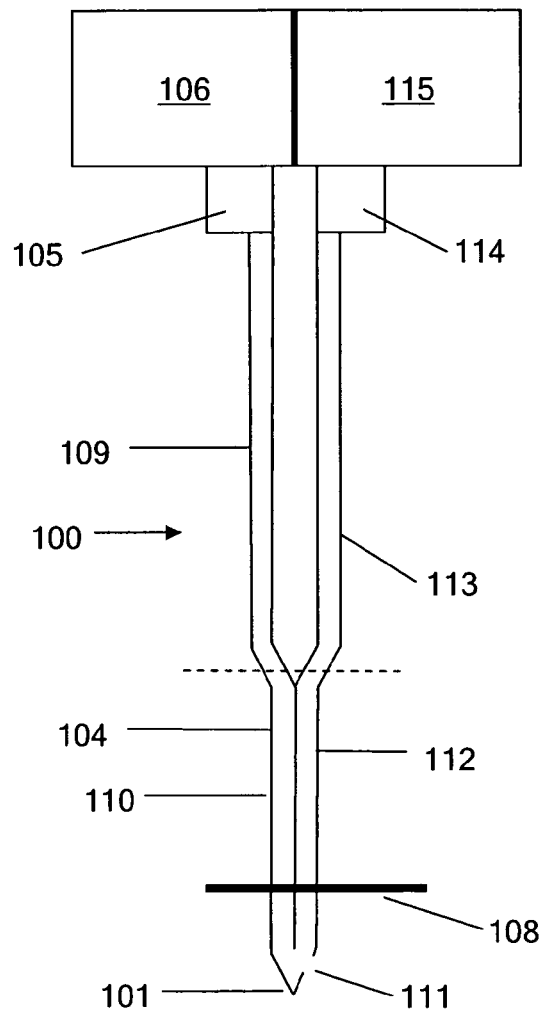
FIGS. 10A and 10B are enlarged side sectional views of embodiments of the invention.
Figure 10B:
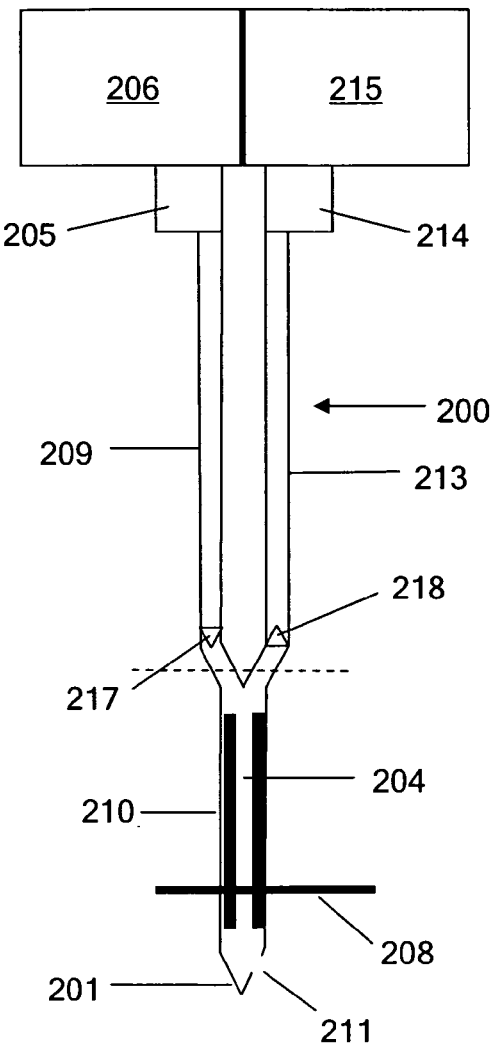

Alternate embodiments of the invention are illustrated in FIGS. 10A and 10B. In FIG. 10A, a two-lumen needle design is shown. Device 100 includes needle 110 having sharpened tip 101 with fluid outlet/inlet 111. Needle 110 is shown inserted through tympanic membrane 108. Needle 110 includes bores 104 and 112, one (bore 104) of which serves as a conduit for delivery of fluids to the middle ear and the other (bore 112) of which serves as a conduit for removal of fluids from the middle ear. Bores 104 and 112 are in fluid communication with lumens 109 and 113, respectively. As shown, lumen 109 is in fluid communication with fluid reservoir 106 via pump 105. Pump 105 controls the delivery of fluids into the middle ear through needle 110, and prevents the undesired return of fluids through bore 104 and lumen 109. Similarly, lumen 113 is in fluid communication with spent fluid reservoir 115 via pump 114. Pump 114 controls the extraction of fluids from the middle ear via needle 110.

In FIG. 10B, a single-lumen needle design is shown. Device 200 includes needle 210 having sharpened tip 201 with fluid outlet/inlet 211. Needle 210 is shown inserted through tympanic membrane 208. Needle 210 includes a single bore 204 which serves as a conduit for delivery of fluids to the middle ear and as a conduit for removal of fluids from the middle ear. Bore 204 in fluid communication with lumens 209 and 213. As shown, lumen 209 is in fluid communication with fluid reservoir 206 via pump 205. Pump 205 controls the delivery of fluids into the middle ear through needle 210. Unidirectional valve 217 prevents the undesired return of fluids through lumen 209. Similarly, lumen 213 is in fluid communication with spent fluid reservoir 215 via pump 214. Pump 214 controls the extraction of fluids from the middle ear via needle 210. Unidirectional valve 218 prevents the return of spent fluid to the middle ear through lumen 213.

A suitable pump is an off-the-shelf drug delivery pump, such as a Disetronic pump, to set, control and adjust drug dosing in the office as indicated by the physician. Throughout the dosing period, if indicated, subject status may be monitored by staff or, alternatively, an head-mounted positional management (HPM) system such as is described in U.S. Pat. No. 6,800,062.

When the invention is used, the tympanic cavity behind the tympanic membrane can act as a circulation reservoir where there is an alternating or pulsating inflow of fresh perfusate and outflow of spent perfusate, thus maintaining the perfusate (solute) concentration that contacts the round window membrane at consistent and optimal levels during the period of perfusion. Thus, this invention allow for a more idealize infusion regime, whereby greater concentrations of a drug can be supplied to the inner ear via a frequent replacement or replenishing of the drug. Fresh perfusate containing a relatively high concentration of the active substances is supplied to the middle ear through the device, where it mixes with spent perfusate, thereby enriching the supply of active substance in the ear. A portion of the spent perfusate is then removed as described. In this way, the concentration of active substance can be maintained at a high level in the middle ear, increasing the rate of absorption. The frequent replenishing of the concentration will result in a much more rapid delivery of the active substance to the inner ear. This reduces treatment time, so the patient often be treated in the office situation with assistance from medical professionals on an outpatient basis, rather than being admitted or self-administering infusion at home.

Figure 8:
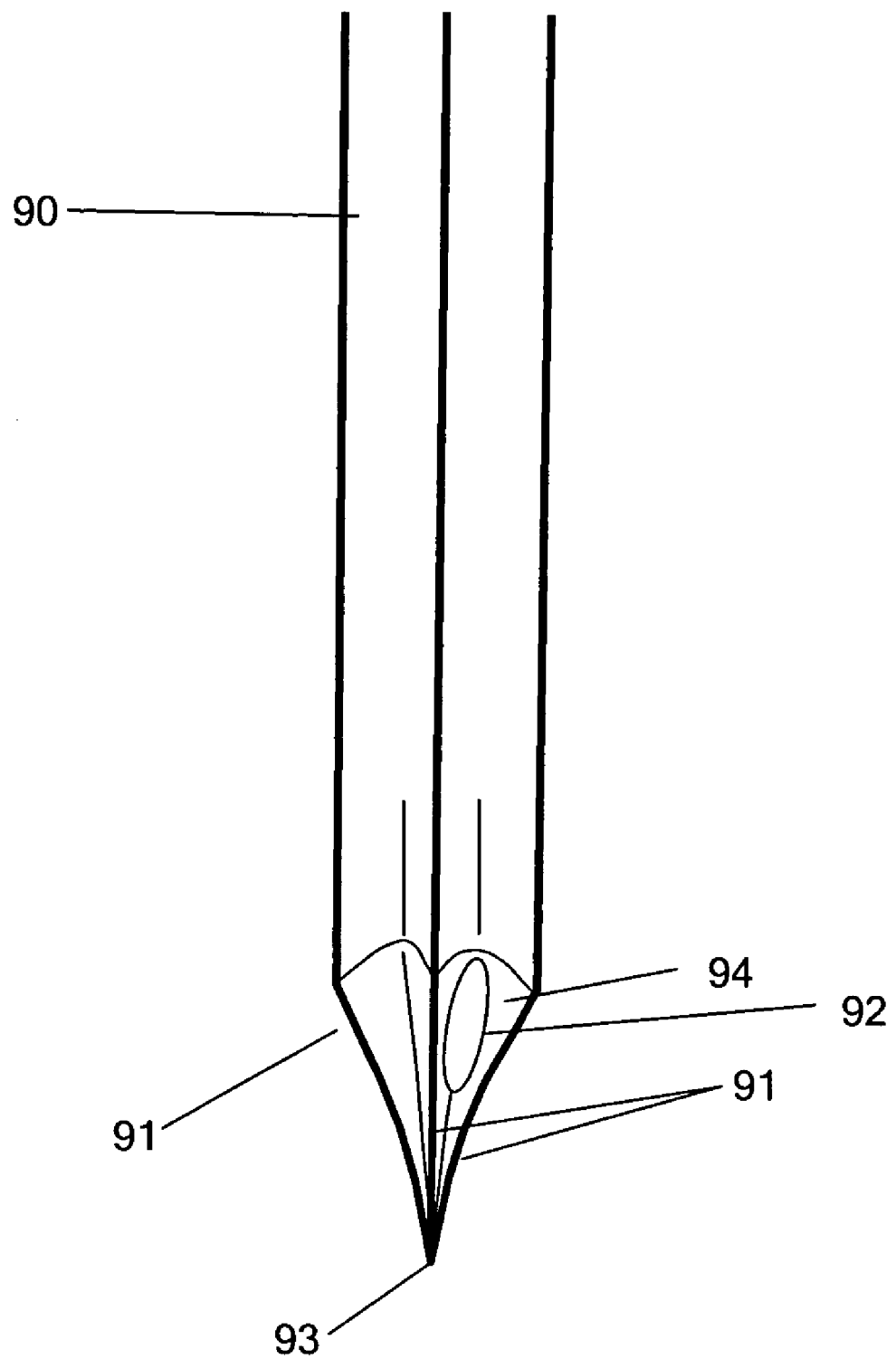
FIG. 8 is an enlarged side view of a preferred needle tip for use with the invention.

A preferred needle design is illustrated in FIG. 8. Needle 90 includes multiple prongs 91 that converge at center point 92. As shown in FIG. 8, needle 90 includes three prongs 91, but a greater number of prongs, such as from 3 to 8 prongs, can be used. The prongs define multiple faces 94 at the tip of needle 91. Fluid outlet 92 extends through one of these faces in the embodiment shown, but it is possible for bore 92 to be placed above the needle tip, so long as it is located within the middle ear when the needle is inserted.

A multicuspid needle tip as shown in FIG. 8 creates multiple incisions extending outward from a central point, thereby forming a corresponding number of skin flaps. These skin flaps are pushed aside upon insertion of the trocar tip through the tympanic membrane. When the trocar tip is removed, these skin flaps can move back into place, thus minimizing healing time, patient discomfort and complications.

As can be seen in FIGS. 5 and 6, a generally illustrated procedure for use of device 36 is shown wherein the trocar end of the device, under the observation of a suitably placed viewing scope 60, is inserted through a slotted speculum 62 into the ear to pierce the tympanic membrane. The slotted speculum 62 is then removed, while still carefully stabilizing the trocar. Following this, and through any suitable device which can eject an appropriate stabilizing and sealing material, the region around body 36a is encapsulated in a flowable and curable sealing substance 64 of any suitable variety, thus to provide local stabilization between the position of the device and the immediately adjacent ear structure. In a preferred embodiment, the device contains external (to the tympanic membrane when inserted) ribs 36e that allow the fixation material to keep the insertion system securely in place after installation and during drug delivery. An inert fixation material, such a curable silicone wax, can be inserted in and around the ear canal and upon solidification fix the trocar and its tubing in place in the external canal, and to seal the canal from possible fluid leakage during the drug delivery procedure.

Manipulation of the device during insertion into the ear and sealing in place, as is illustrated in FIG. 6, is accommodated by digital manipulation utilizing bead 36c while the hand is stabilized against the head.

Figure 9:
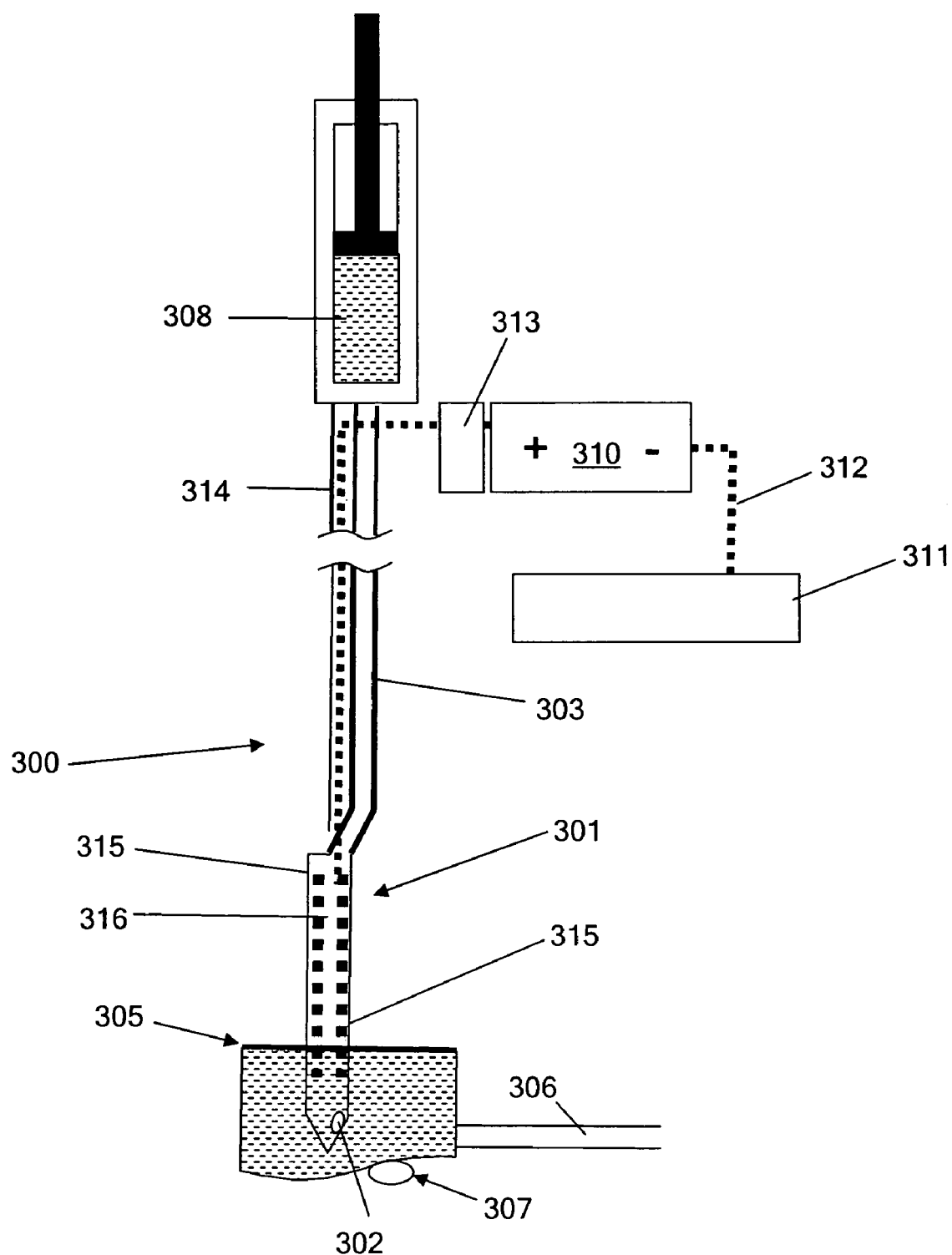
FIG. 9 is a side schematic view of an embodiment of the invention.

FIG. 9 illustrates yet another embodiment of the invention, in which iontophoresis can be applied with the delivery of fluids to the middle ear. Device 300 includes needle 301 having, in the embodiment shown, a single bore 316, which is in fluid communication with fluid outlet 302 and lumen 303. Lumen 303 is in fluid communication with fluid reservoir 308, which in this embodiment is shown as a simple syringe. Pumps and valves can be used in connection with this embodiment of the invention, in the general manner described before (see FIGS. 10A and 10B, for example). Device 300 is shown in FIG. 9 inserted in its proper position with needle 301 penetrating tympanic membrane 305 so fluid outlet 302 resides within the inner ear. The round window membrane is shown schematically at 307 and the Eustachian tube is shown schematically at 306.

In this embodiment, the exterior surfaces of needle 301 are preferably made of a non-conductive material. Within bore 316 of needle 301 resides electroconductive material 315, which is in electrical communication with one (typically the positive) electrode of electrical power source 310 via circuit 314, and is also in contact with fluid residing in bore 316 of needle 301. Circuit 414 and lumen 403 are generally retained within a single catheter. The other (typically the negative) electrode of electrical power source 310 is in electrical communication with body electrode 311, which during operation is applied to the skin of the patient. As shown, a controller 313 controls operation of the electrical power supply to device 300. Iontophoresis is applied though the single-lumen catheter via an electrode that contacts the fluid in the lumen of the needle. The needle in this case is non-metallic and non-conductive on the outside, but conductivity is supplied to the inside. The negative electrode is applied to the skin. The applied and controlled current forms positively-charged ions within the active substance. The round window membrane becomes oppositely charged, thereby attracting the positively-charged ions and facilitating their transport to and through the round window membrane. As this is taking place, the perfusate ions are constantly replenished via the catheter, and the spent fluid can pass through the Eustachian tube (ET).

Figure 11:
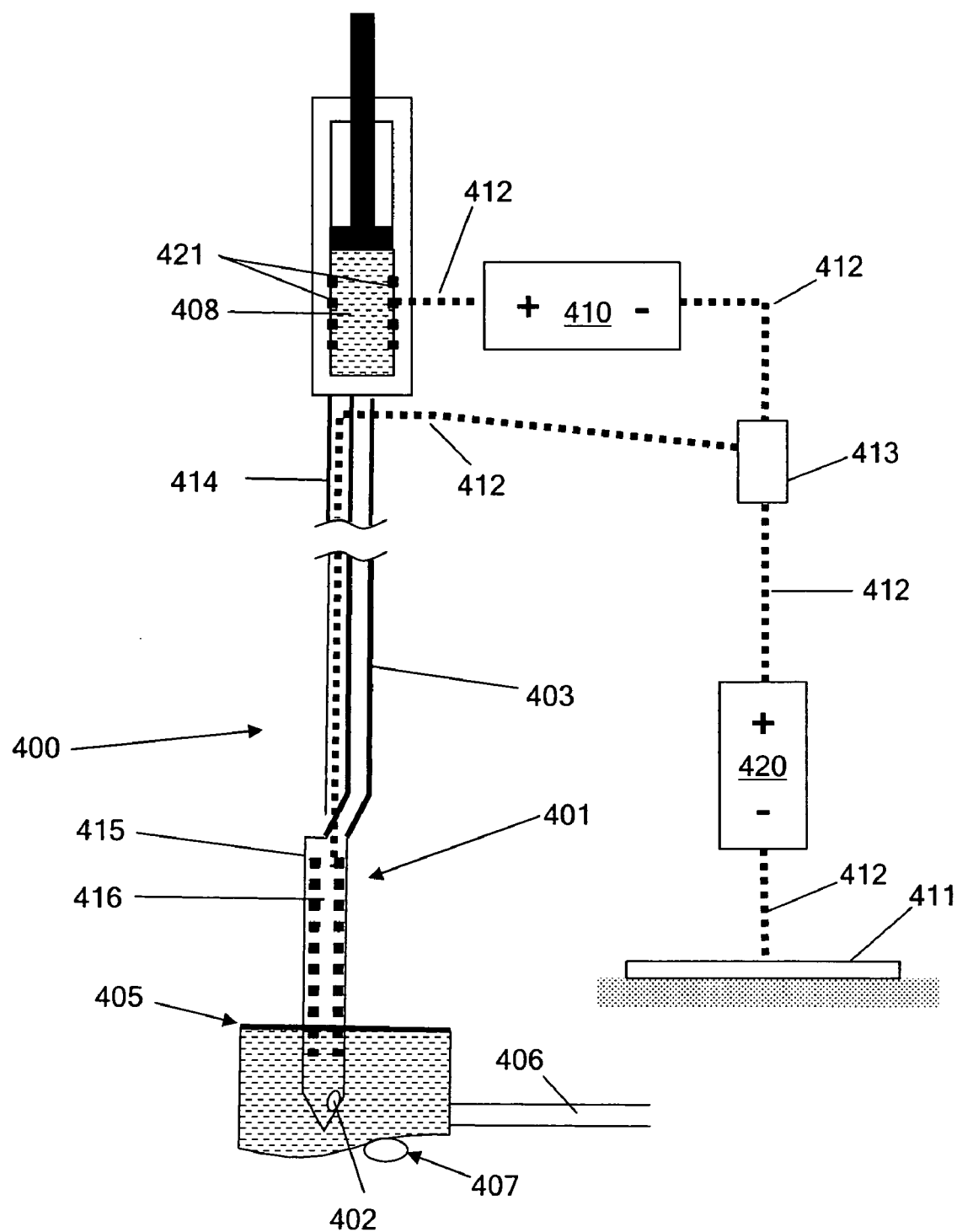
FIG. 11 is a side schematic view of an embodiment of the invention.

FIG. 11 illustrates another embodiment of the invention in which iontophoresis can be applied with the delivery of fluids to the middle ear. Device 400 includes needle 401 having, in the embodiment shown, a single bore 416, which is in fluid communication with fluid outlet 402 and lumen 403. Lumen 403 is in fluid communication with fluid reservoir 408, which in this embodiment is shown as a simple syringe. Pumps and valves can be used in connection with this embodiment of the invention, in the general manner described before (see FIGS. 10A and 10B, for example). Device 400 is shown in FIG. 11 inserted in its proper position with needle 401 penetrating tympanic membrane 405 so fluid outlet 402 resides within the inner ear. The round window membrane is shown schematically at 407 and the Eustachian tube is shown schematically at 406.

In this embodiment, ionizing current is supplied in two stages, first within fluid reservoir 408 and again within needle 401. Ionizing current is supplied to needle 401 in the same manner as described with respect to the embodiment shown in FIG. 9. Electroconductive material 415 resides within bore 416 of needle 401 and is in electrical communication with one (typically the positive) electrode of electrical power source 420 via circuit 412 and 414, and is also in contact with fluid residing in bore 416 of needle 401. Circuit 414 and lumen 403 are generally retained within a single catheter. In this embodiment, ionizing current is also supplied to fluid within fluid reservoir 408 through electrodes 421, which are in electrical communication with electrical power source 410 via circuit 412. As shown, both electrical power source 410 and 420 are controlled through a single controller 413, but multiple controllers can be used if desired. Alternatively, a single electrical power source may provide current to both electrodes 421 and electroconductive material 415. As before, the other (typically the negative) electrode of an electrical power source (either 410 or 420, or both) is in electrical communication with body electrode 411 via circuitry 412, which during operation is applied to the skin of the patient. Iontophoresis is applied to the fluid through both electrodes 421 and electroconductive materials 415. As before, needle 401 is non-metallic and non-conductive on the outside, but conductivity is supplied to the inside. The round window membrane becomes oppositely charged, thereby attracting the positively-charged ions and facilitating their transport to and through the round window membrane. As this is taking place, the perfusate ions are constantly replenished via the catheter, and the spent fluid can pass through the Eustachian tube (ET).

Although FIG. 11 describes a two-stage iontophoretic device, the device may contain any number of electrodes to create any desired number of stages.

The embodiments illustrated in FIGS. 9 and 11 each can be modified in various ways. The needle point may be a multi-cuspid type as described herein. A dual-bore needle as described in FIGS. 7 and 10A may be used, together if desired with an associated lumen and optional pump and/or reservoir to permit spent perfusate to be removed through the needle as described before. Such an embodiment permits alternating supply of fresh perfusate and withdrawal of spent perfusate as described before. A single bore needle can also be used with the embodiment illustrated in FIG. 9, in which the needle is adapted to permit the supply of fresh perfusate and withdrawal of spend perfusate. For example, a single bore needle may be used in combination with a lumen and optional pump and/or reservoir in a manner analogous to the embodiment shown in FIG. 10B.

The device of the invention typically will require only a brief in-office procedure under topical anesthesia for placement in the ear. The device will make a minimal incision in the tympanic membrane that can heal in significantly less time than with existing methods. The device of the invention is designed to remain in the ear for a period of up to 8 hours or more, with delivery of the drug or other fluid at a set dosing rate and pattern.

As is generally illustrated in FIG. 1 in the drawings, an appropriate way of anchoring a device 34 or a device 36 to frame structure 22 may be some suitable form of releasable clamp mechanism which allows snap fitting of a region of the tubular bodies in these two devices to the outer side, or sides, of band 26 in the frame structure. Again, the specific manner of anchoring attachment and stabilization are matters of user choice.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that embodiments of the methods and system of the invention may be implemented by a computer or microprocessor process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

I claim:

1. An iontophoretic system for delivering medically-active ions in solution to a middle ear of a patient, comprising:
   a needle, wherein the needle is configured to enable one or both of delivering a fluid to and removing fluid from a middle ear of a patient, the needle comprising:
      a sharpened end configured to pierce a tympanic membrane and for insertion through the tympanic membrane of the ear; wherein the sharpened end of the needle includes multiple sharpened knife-like edges radiating outward from a common central sharpened point, the edges presented outwardly from a longitudinal axis of the needle and configured when inserted through the tympanic membrane to form multiple membrane flaps;

an opposite end, at least one longitudinal bore configured to extend between the opposite end and the sharpened end, and a fluid outlet proximate to the sharpened end and in fluid communication with the at least one longitudinal bore;

a flexible lumen in fluid communication with the at least one longitudinal bore and having a first end configured to operatively couple with the opposite end of the needle and having a second end configured to operatively couple with a fluid source; and iontophoretic means configured with at least an anode and a cathode to deliver medically-active ions through the needle to the middle ear.

2. The system of claim 1, wherein substantial portions of an exterior surface of the needle are formed of an electrically nonconductive material, are covered by an electrically nonconductive material, or comprise a combination thereof.

3. The system of claim 1, wherein the iontophoretic means comprises:

one or more electrical power sources configured to supply an electrical current;

at least a first electrically-conductive material operatively coupled with a first electrode of the one or more electrical power sources and provided either within or as a part of the longitudinal bore; and at least a second electrically-conductive material configured to attach to the patient's skin and operatively coupled with a second electrode of the one or more power sources, wherein the second electrode is configured for an opposite electrical charge relative to the first electrode.

4. The system of claim 1, wherein the iontophoretic means includes electrically-conductive means for supplying an ionizing electrical charge to a fluid residing within the longitudinal bore, the flexible lumen, or both, and means for applying an opposite electrical charge to a patient's body such that iontophoresis of medically active ions is induced from the fluid provided through the needle to a round window membrane of the patient's middle ear.

5. The system of claim 4, wherein the means for supplying an ionizing electrical charge comprises multiple electrodes residing within any one of or collectively within a combination selected from the group consisting of the longitudinal bore, the flexible lumen, and a fluid reservoir in fluid communication with the flexible lumen.

6. The system of claim 5, wherein the electrodes are configured to provide an ionizing electrical charge in two or more stages and to provide a contiguous electromotive force gradient as a voltage drop sequentially toward the middle ear.

7. The system of claim 2, wherein the needle further comprises a positioning tab operatively coupled with the exterior of the needle and configured to contact a surface of the tympanic membrane external to the middle ear and to establish a maximum insertion extent of the sharpened end of the needle through the tympanic membrane, and wherein substantial portions of an exterior surface of the positioning tab are formed of an electrically nonconductive material, are covered by an electrically nonconductive material, or comprise a combination thereof.

8. An iontophoretic method for delivering medically-active ions in solution to a middle ear of a patient, comprising:

imparting a positive electrical charge to medically-active ions of a fluid by operatively coupling an anode of a power source with the fluid;

imparting a negative electrical charge to a round window membrane of a middle ear of a patient by operatively coupling a cathode of the power source to the patient;

inserting a portion of a needle through a tympanic membrane of the patient so that a sharpened end of the needle and a fluid outlet proximate to the sharpened end are presented within the middle ear; wherein the sharpened end of the needle includes multiple sharpened knife-like edges radiating outward from a common central sharpened point, the edges presented outwardly from a longitudinal axis of the needle and configured when inserted through the tympanic membrane to form multiple membrane flaps;

providing the fluid to the middle ear through the fluid outlet via a longitudinal bore of the needle in fluid communication with the fluid outlet; and iontophoretically delivering the medically-active ions to one or both of the round window membrane and a portion of an inner ear separated from the middle ear by the round window membrane.

9. The method of claim 8, wherein delivering the medically-active ions comprises maintaining an elevated concentration of positively-charged, medically-active ions within the middle ear by sequentially providing fresh fluid via the needle and evacuating spent fluid via a Eustachian tube of the patient.

10. The method of claim 8, wherein substantial portions of an exterior surface of the needle are formed of an electrically nonconductive material, are covered by an electrically nonconductive material, or are formed and covered according to a combination thereof.

11. The method of claim 8, further comprising one of:

providing the anode within a structure or within two or more of a contiguous combination of structures selected from the group consisting of the longitudinal bore, a fluid reservoir in fluid communication with the longitudinal bore, and a flexible lumen in fluid communication with the longitudinal bore; or providing the anode as one of a plurality of anodes within one of or any combination of structures selected from the group consisting of the longitudinal bore, a fluid reservoir in fluid communication with the longitudinal bore, and a flexible lumen in fluid communication with the longitudinal bore.

12. The method of claim 10, further comprising:

providing a positioning tab operatively coupled with the exterior surface of the needle and configured to contact a surface of the tympanic membrane external to the middle ear when the needle is inserted through the tympanic membrane, and further configured to delimit the portion of the needle to be inserted through the tympanic membrane, wherein substantial portions of an exterior surface of the positioning tab are formed of an electrically nonconductive material, are covered by an electrically nonconductive material, or comprise a combination thereof.

13. An iontophoretic intra-tympanic drug delivery apparatus, comprising:

a fluid delivery portion comprising, a needle having a sharpened end, an opposite end, a longitudinal bore extending from the sharpened end to the opposite end, and a fluid outlet from the longitudinal bore disposed proximate the sharpened end, wherein the sharpened end of the needle includes multiple sharpened knife-like edges radiating outward from a common central sharpened point, the edges presented outwardly from a longitudinal axis of the needle and configured when inserted through the tympanic membrane to form multiple membrane flaps;

a positioning tab coupled with an exterior portion of the needle between the sharpened end and the opposite end and configured to contact a surface of a tympanic membrane of a patient when the sharpened end of the needle is inserted therethrough, and a flexible lumen operatively coupled with the opposite end and in fluid communication with the longitudinal bore; and an iontophoretic portion, comprising, one or more power sources, a first current-carrying means operatively coupled with a first electrode of the one or more power sources, and a first electrically-conductive material operatively coupled with the first current-carrying means; the first electrically-conductive material being configured during use to be located within, and to be in electrically-conductive contact with a fluid within, one or more selected from the group consisting of the flexible lumen, the longitudinal bore, or a fluid reservoir operatively coupled with and in fluid communication with the flexible lumen.

14. The apparatus of claim 13, wherein the iontophoretic portion further comprises:

a second current-carrying means operatively coupled with a second electrode of the one or more power sources, and a second electrically-conductive material operatively coupled with the second current-carrying means and configured to operatively couple with skin of the patient.

15. The apparatus of claim 13, wherein a substantial exterior portion of the needle, the positioning tab, or both is/are formed of an electrically-nonconductive material, is covered with an electrically-nonconductive material, or is a combination of so covered and so formed.

16. The apparatus of claim 14, wherein one of the first or the second electrode is an anode, and the other of the first or the second electrode is a cathode, and the apparatus is configured to form a current-carrying electrical circuit when operatively coupled with a patient and when a fluid comprising medically-active ions is operatively disposed through the fluid delivery means into a middle ear of the patient.

17. The apparatus of claim 13, wherein the sharpened end of the needle includes multiple sharpened knife-like edges radiating outward from a common central sharpened point, the edges presented outwardly from a longitudinal axis of the needle and configured when inserted through the tympanic membrane to form multiple membrane flaps with cleanly incised reciprocal margins.

18. The apparatus of claim 13, further comprising:

one or more controllers operatively coupled with the current-carrying means and configured to modulate an electrical current supplied to the current-carrying means from the one or more power sources.

* * * * *